United States Patent
Wong

(10) Patent No.: US 12,220,501 B1
(45) Date of Patent: Feb. 11, 2025

(54) INJECTABLE HYDROGEL FOR TREATMENT OF SEGMENTAL BONE DEFECT

(71) Applicant: TAIPEI MEDICAL UNIVERSITY, Taipei (TW)

(72) Inventor: Chin-Chean Wong, Taipei (TW)

(73) Assignee: TAIPEI MEDICAL UNIVERSITY, Taipei (TW)

(*) Notice: Subject to any disclaimer, the term of this patent is extended or adjusted under 35 U.S.C. 154(b) by 0 days.

(21) Appl. No.: 18/239,216

(22) Filed: Aug. 29, 2023

(30) Foreign Application Priority Data

Jul. 26, 2023 (TW) .................................. 112127852

(51) Int. Cl.
*A61L 27/52* (2006.01)
*A61L 27/26* (2006.01)
*A61L 27/36* (2006.01)
*A61L 27/48* (2006.01)
*A61L 27/54* (2006.01)

(52) U.S. Cl.
CPC .............. *A61L 27/52* (2013.01); *A61L 27/26* (2013.01); *A61L 27/3616* (2013.01); *A61L 27/365* (2013.01); *A61L 27/48* (2013.01); *A61L 27/54* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| 2013/0236513 A1* | 9/2013 | Guelcher | A61K 38/1875 |
| | | | 514/769 |
| 2022/0133896 A1* | 5/2022 | Duan | A61K 47/61 |
| | | | 424/409 |

FOREIGN PATENT DOCUMENTS

| CN | 103007345 A | 4/2013 |
| CN | 104582747 A | 4/2015 |
| WO | WO-2022082027 A1 * | 4/2022 | ........... A61K 35/745 |

OTHER PUBLICATIONS

Antich et al., Acta Biomaterials 106 (2020) 114-123 (Year: 2020).*
Collins Dictionary definition: Ambient Temperature, retrieved from the internet:https://www.collinsdictionary.com/us/dictionary/english/ambient-temperature (Year: 2024).*

(Continued)

*Primary Examiner* — Evelyn Y Pyla
(74) *Attorney, Agent, or Firm* — Demian K. Jackson; Jackson IPG PLLC

(57) ABSTRACT

The invention relates to an injectable hydrogel composition of 10 wt % gelatin, 0.5-2 wt % hyaluronic acid, 0.5-1.0 wt % genipin and an aqueous medium. The composition exhibits high biocompatibility, injectability and in-situ gelation ability at bone defect sites. The composition is suitable for serving as an osteogenic scaffold for cell adhesion and as an osteogenic carrier for delivering beneficial substance for promoting bone regeneration. The invention also relates to a medical formulation comprising the injectable hydrogel composition in combination with an osteogenic substance, as well as the medical use thereof in the treatment of segmental bone defect.

10 Claims, 18 Drawing Sheets

(56) References Cited

OTHER PUBLICATIONS

Millipore, 69966 MRS Broth, www.sigmaaldrich.com, retrieved from the internet (Jun. 28, 2024): https://www.sigmaaldrich.com/US/en/specification-sheet/SIAL/69966 (Year: 2024).*

Sigma Aldrich, Gelatin from bovine skin #G9391, retrieved from the internet (Jun. 28, 2024): https://www.sigmaaldrich.com/US/en/product/sigma/g9391 (Year: 2024).*

Study.com, definition of Ambient Temperature, retrieved from the internet (Jun. 28, 2024): https://study.com/academy/lesson/ambient-temperature-definition-range.html#:~:text=Ambient%20temperature%20is%20the%20average,is%20not%20always%20room%20temperature. (Year: 2024).*

Teixeira et al., International Journal of Molecular Sciences, 2022, 23, 6564, pp. 1-46 (Year: 2022).*

Khatun et al., Bioresponsive Gelatin-Hyaluronic Acid Hydrogels for 3D Bioprinting, obtained online at Preprints.org, posted Jun. 29, 2023, pp. 1-15. (Year: 2023).*

Ng et al., In vitro evaluation of genipin-crosslinked gelatin hydrogels for vocal fold injection, Scientific Reports (2023) 13:5128, pp. 1-12 (Year: 2023).*

Search Report for corresponding applicationTW112127852 mailed Oct. 26, 2023.

Zhang et al., "Advancements in Hydrogel-Based Drug Sustained Release Systems for Bone Tissue Engineering" Frontiers in Pharmacology 2020, 11, Article 622.

Bai et al., "Bioactive Hydrogels for Bone Regeneration" Bioactive Materials 2018, 3, 401-417.

* cited by examiner

INJECTABLE HYDROGEL FOR TREATMENT OF SEGMENTAL BONE DEFECT

CROSS REFERENCE TO RELATED APPLICATION

This application claims priority to R.O.C. Patent Application No. 112,127,852 filed Jul. 26, 2023, which is hereby incorporated by reference in its entirety.

FIELD OF THE INVENTION

The invention relates to an injectable hydrogel composition that is derived from natural sources and exhibits high biocompatibility, injectability and in-situ gelation ability at bone defect sites. The invention also relates to a medical formulation comprising the injectable hydrogel composition in combination with an osteogenic substance, as well as the medical use thereof in the treatment of segmental bone defect.

DESCRIPTION OF THE RELATED ART

Segmental bone defects refer to a partial or circumferential absence of bone tissues at defect sites, usually being attributed to high-energy trauma, tumor resection, skeletal reconstructions, infections, developmental deformities or osteomyelitis. In the cases of so-called "critical" segmental bone defects, the areas of bone loss are so large that the defects may cause significant patient morbidity and will fail to heal and result in delayed union or non-union of bone tissue without medical intervention. While bone grafting and internal/external fixation have been used widely as the main therapeutic strategy in the defect-filling applications, healing of segmental bone defects remains an enormous challenge in clinical orthopedics. Various tissue engineering approaches have been proposed to facilitate segmental bone healing, including implantation of osteoconductive scaffolds and delivery of osteoinductive growth factors and osteogenic cells. A common approach is to use poly (methyl methacrylate)-based bone cement as a scaffold. While the PMMA bone cement has the advantages of possessing high compressive strength and good ability to bond to bone tissue, it is not biodegradable and usually needs to be removed from the defect site through a secondary surgery, which may pose additional risks to the patient. In addition, the non-biodegradability of PMMA bone cement can also lead to long-term complications such as stress shielding, where the surrounding bone may weaken due to lack of mechanical loading, and the cement may also cause chronic inflammation. As an alternative approach, hydrogels have gained growing attention as they are promising candidates for use as three-dimensional osteogenic scaffolds for cell adhesion and as osteogenic carriers for delivery of cells, stimulating factors or medicaments (for review articles, please see, for example, Bai, X. et al., *Bioactive Materials*, (2018), 3: 401-417; Zhang Y.-F. et al., *Front Pharmacol.*, (2020) 11:622).

Hydrogels are viscoelastic polymeric material with highly hydrated three-dimensional crosslinked networks mimicking bone extracellular matrices (ECM) and providing an appropriate microenvironment for bone regeneration. Hydrogels may be derived from protein-based or polysaccharide-based natural biomaterials, such as gelatin, collagen, chitosan and hyaluronic acid, synthetic polymers, such as polyethylene glycol, polyacrylamide, polyvinyl alcohol, and their hybrid combinations. By virtue of their excellent biocompatibility, non-cytotoxicity and biodegradability, natural hydrogels are often preferred over synthetic hydrogels in tissue engineering applications. Gelatin-based hydrogels are among the most commonly used natural hydrogels for bone tissue engineering. Gelatin is a hydrolyzed product of collagen—the main structural protein in the ECM of bone tissue, and can be functionalized via its reactive amino groups. However, as it tends to dissolve spontaneously at the physiological temperature and therefore shows insufficient mechanical properties to support bone regeneration, gelatin is not suitable for use alone in the treatment of segmental bone defects where high mechanical stability is required. The gelation times of gelatin hydrogels should also be adjusted to suit the specific needs for the treatment of segmental bone defects. That is to say, the gelatin hydrogel need be tailored to have a suitable gelation time that allows for easy injection into the bone defect site during a surgical procedure while ensuring that it transitions into a gel state at the defect site within an appropriate time frame, typically around 30 minutes, to allow orthopedists to complete the surgical procedure. Theoretically, the mechanical properties and gelation time of a gelatin hydrogel can be adjusted through various means such as modifying the chemical composition of the hydrogel, adjusting the degree of cross-linking and incorporating additional materials. In practice, however, it remains unsuccessful to fabricate a hydrogel formulation which meets all of the requirements described above.

While gelatin-based hydrogels have shown promise in the art, there is still a need for developing an improved biomaterial and method for treatment of segmental bone defect.

SUMMARY OF THE INVENTION

In order to fulfill the need above, the inventor has developed a gelatin-based hydrogel composition, in which all of the hydrogel precursors are essentially derived from natural sources and thus exhibit excellent biocompatibility with patients. In terms of chemical composition, the hydrogel composition herein includes a blend of gelatin and hyaluronic acid in combination with a specific concentration of genipin as a cross-linking agent to constitute an injectable formulation. The precursor combination remains in a generally liquid state at ambient temperature before being injected into the bone defect site but is adapted to undergo transition into gel state under physiological conditions, such as at about 37° C. and pH 7.0, within 10-40 minutes, such as between 20-30 minutes. Such injectability and in-situ gelation ability are crucial properties for the treatment of segmental bone defect, as they make the hydrogel herein deliverable directly to the defect site through minimally invasive procedures and minimize the risk of infection and other complications. By virtue of adding the particular amount of genipin, the mechanical properties and the in-situ gelation time of the hydrogel herein are tuned to provide structural support for bone growth and regeneration in segmental bone defects while also serving as a carrier for delivery of osteogenic substances.

Accordingly, in the first aspect provided herein is an injectable hydrogel precursor composition comprising, preferably consisting essentially of, and more preferably consisting of:

about 10% by weight of gelatin, based on the total weight of the composition;

about 0.5-2% by weight of hyaluronic acid, based on the total weight of the composition;

about 0.5-1.0% by weight of genipin, based on the total weight of the composition; and an aqueous medium having a pH ranging from 6-8;

wherein the injectable hydrogel precursor composition is adapted to transition into a hydrogel at 37° C. with a gelation time ranging from 10 minutes to 40 minutes while remaining injectable at ambient temperature for at least 60 minutes, and the hydrogel has a compressive strength ranging from 300 kPa to 500 kPa.

In the second aspect provided herein is a medical formulation comprising the injectable hydrogel precursor composition above in combination with an osteogenic substance selected from the group consisting of a mesenchymal stem cell, a stem cell secretome, a platelet-rich fibrin, a platelet-rich plasma, a chemotherapeutic drug, a growth factor, a cytokine, an antibiotic and a combination thereof.

In the third aspect provided herein is use of the medical formulation described above in the manufacture of a medicament for treatment of a segmental bone defect having a defect site between a first bone end and a second bone end disconnected to the first bone end.

In the fourth aspect provided herein is a method for treating a segmental bone defect having a defect site between a first bone end and a second bone end disconnected to the first bone end, comprising injecting the medical formulation described above to the defect site and allowing the medical formulation to transition to a hydrogel in situ.

In the preferred embodiments, hyaluronic acid is in an amount of about 1% by weight based on the total weight of the composition, and genipin is in an amount of about 0.5% by weight based on the total weight of the composition. In more preferred embodiments, the hyaluronic acid has a molecular weight of between about 8,000 kDa to about 10,000 kDa.

In the preferred embodiments, gelatin is selected from the group consisting of type-A gelatin, type-B gelatin, and a combination thereof. In more preferred embodiments, the gelatin comprises type-B gelatin.

In the preferred embodiments, the aqueous medium is selected from the group consisting of water, water-based solutions and water-based buffers.

BRIEF DESCRIPTION OF THE DRAWINGS

The above and other objects, features and effects of the invention will become apparent with reference to the following description of the preferred embodiments taken in conjunction with the accompanying drawings, in which.

DETAILED DESCRIPTION OF THE INVENTION

Figure 1:
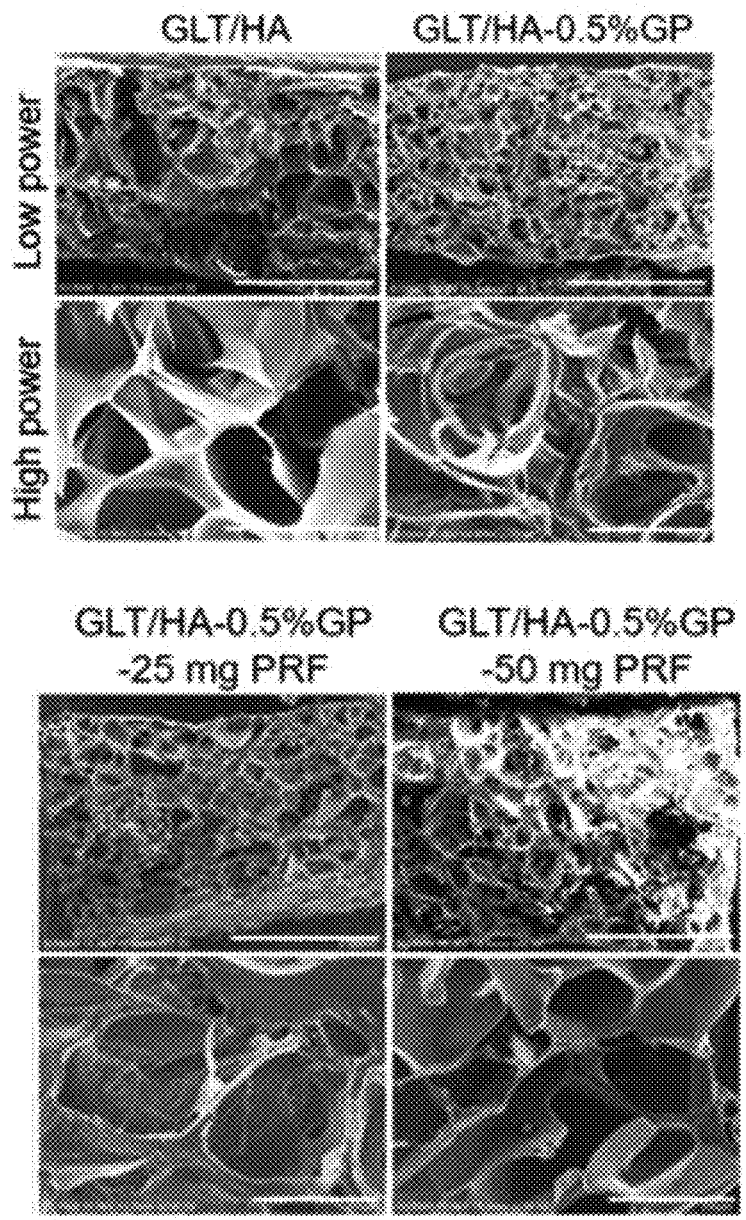
FIG. 1 shows scan electron microscopic images of the hydrogels according to the invention.

Unless specified otherwise, the following terms as used in the specification and appended claims are given the following definitions. It should be noted that the indefinite article "a" or "an" as used in the specification and claims is intended to mean one or more than one, such as "at least one," "at least two," or "at least three," and does not merely refer to a singular one. In addition, the terms "comprising/ comprises," "including/includes" and "having/has" as used in the claims are open languages and do not exclude unrecited elements. The term "or" generally covers "and/or", unless otherwise specified. The term "about" used throughout the specification and appended claims is used to describe and account for slight changes that do not materially affect the nature of the invention.

As used herein, the term "hydrogel" refers to a three-dimensional polymeric network of gelatin and hyaluronic acid crosslinked covalently by genipin and hydrated by an aqueous medium. The term "hydrogel precursor composition" as used herein may refer to a mixture of about 10 wt % gelatin, about 0.5-2 wt % hyaluronic acid and about 0.5-1.0 wt % genipin in the aqueous medium, which is in form of an injectable fluid and is adapted to transition into a hydrogel through crosslinking under physiological conditions, namely at about 37° C. and pH 7. Alternatively, the composition may be present in form of two or more separate parts to be mixed prior to use, so as to prevent premature gelation. The term "injectable" means that the composition herein has sufficient flowability to be delivered to a patient with an injection device, such as a syringe and a cartridge.

In preferred embodiments, the composition is suitable for administration to a segmental bone defect site through injection.

As used herein, the term "gelatin" or abbreviated as "GLT" is intended to encompass all of the protein substances obtained by acid, alkaline or enzymatic hydrolysis of collagen taken from skin, bones and connective tissues of animals. Compared with collagen, GLT exhibits higher biocompatibility, biodegradability, cost effectiveness, low immunogenicity, and easy-to-obtain properties. GLT is rich in glycine, proline and hydroxyproline in terms of primary structure and, therefore, is suitable for cell attachment and growth, and maintenance of the physiological functions of cells. The GLT useful in the invention may include, but be not limited to, type-A GLT which is derived from porcine, poultry or fish source and has an isoelectric point of 7.0-9.0, type-B GLT which is derived from bovine skin and has an isoelectric point of about 5.0, and a combination thereof. In preferred embodiments, there is only type-B GLT contained in the hydrogel precursor composition. In the context of the invention, the amount of GLT contained in the composition herein is about 5 wt % to about 20 wt %, and more preferably about 10 wt %, based on the total weight of the composition.

The term "hyaluronic acid" or "hyaluronan", or abbreviated as "HA", is used herein to encompass a linear glycosaminoglycan polymer composed of repeating units of N-acetyl D-glucosamine and D-glucuronic acid with the monosaccharide units linked together via alternating −1,3 and −1,4 glycosidic bonds, as well as alkali metal salts thereof, including sodium, potassium and lithium salts thereof. Preferably, the HA used herein has a molecular weight of at least about 1,000 kDa, and more preferably has a molecular weight of between about 5,000 kDa to about 50,000 kDa, such as having a molecular weight of between about 8,000 kDa to about 10,000 kDa. The amount of HA contained in the hydrogel precursor composition herein is about 0.5 wt % to about 5 wt %, and more preferably from about 0.5 wt % to about 2.0 wt %, based on the total weight of the composition. Because a certain portion of GLT in the composition may start to gel at ambient temperature and reduce the flowability of the composition, the presence of the specified amount of HA in the composition is crucial for maintaining the injectability of the composition. Without wishing to be bound by a particular theory, it is believed that highly hydrophilic HA can enhance the overall solubility of the hydrogel precursors in the aqueous medium and may be distributed randomly among and interlace with GLT molecules, by which the GLT molecules are no longer arranged in a regular manner, and the flowability of the composition is increased accordingly.

The term "genipin", or abbreviated as "GP", is used herein to refer to a chemical compound found in *Genipa americana* fruit extract and having the following chemical structure:

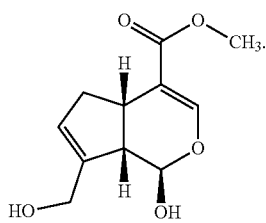 [SMILES: COC(=O)C1=CO[C@@H](O)[C@@H]2C(CO)=CC[C@H]12]

GP is known to be a naturally occurring cross-linker for proteins and chitosan. It exhibits a low toxicity to mammals, with $LD_{50}$ (intravenous) 382 mg/kg in mice, and therefore is much less toxic than glutaraldehyde and many other commonly used synthetic crosslinking reagents. The amount of GP contained in the hydrogel precursor composition herein is about 0.1 wt % to about 1.0 wt %, more preferably from about 0.5 wt % to about 1.0 wt %, and most preferably about 0.5 wt %, based on the total weight of the composition.

As used herein, the term "aqueous medium" is intended to encompass water, such as distilled water, and water-based solutions or buffers, such as normal saline and phosphate buffered saline (PBS). In one embodiment, the aqueous medium has a pH of 6-8, such as about 7.

The term "comprise" or "comprising", when used in a claim, means the elements recited, or their equivalents in structure or function, plus any other element or elements which are not recited. The transitional phrase "consist of" or "consisting of" is closed, and excludes all additional elements. The phrase "consist essentially of" or "consisting essentially of", with respect to the constitutive elements of the composition defined in the claims, means that the composition contains the indicated elements and may contain additional elements only if the additional elements do not materially alter the basic and novel characteristics of the invention as a composition for treatment of segmental bone defect. Preferably, such additives are not present at all or only in trace amounts. For instance, a claimed composition consisting essentially of GLT, HA, GP and an aqueous medium would not exclude trace contaminants from the preparation steps of the substances, such as preservatives and salts, which do not materially affect the injectability and in-situ gelation ability of the precursor composition, as well as the osteoconductive and osteoinductive properties of the hydrogel cured from the composition for the treatment of a segmental bone defect.

The injectable hydrogel precursor composition can be prepared by mixing GLT, HA and GP thoroughly with the aqueous medium. In one embodiment, GLT, HA and GP may be added to the aqueous medium together at ambient temperature under agitation, such as under constant stirring. In another embodiment, GLT and HA may be dissolved in the aqueous medium at higher temperature until a clear solution is obtained, followed by suspending GP in the solution at ambient temperature before use. According to the invention, the composition herein, even when all of the constitutive elements are combined, will still maintain high flowability at ambient temperature to ensure high injectability and is adapted for translation to a hydrogel upon increasing the temperature to 37° C. More importantly, the sol-gel transition of the composition herein occurs and completes within a time interval between 10-40 minutes 37° C., indicating that the composition has a gelation time between 10-40 minutes at the physiological temperature, such as between 20-30 minutes. The term "gelation time" is defined herein as the time needed to reach the gel point of the composition counted from the time point when GP is added into the composition to initiate the crosslinking reaction. In one embodiment, a gelation time may refer to the time needed for the storage modulus (G') of the composition to crossover the loss modulus (G") thereof after the addition of GP, as measured by a rheometer, as illustrated in Example 4 below. In another embodiment where the bottle inversion method is used, a gelation time may refer to the time required for the composition, in an inverted state, shows no considerable fluidity. As shown in Example 5 below, the composition herein, when all of the constitutive elements are mixed together, will remain injectable at ambient temperature for at least an hour, which allows orthopedists to have ample time to complete the surgical procedure, and will rapidly undergo phase transition into gel form under physiological temperature. Such gelation kinetics are particularly advantageous for the treatment of a segmental bone defect, as they provide a workable time window that allows applying the composition to the defect site through an injection device and further makes the composition usable for in-situ gel formation during surgery.

The hydrogel formed from the composition herein has sufficient mechanical strength and stiffness to maintain its structural stability to serve as scaffolding material and provide support for bone regeneration to avoid stress shielding, subsequent bone loss and refracture, while also being able to withstand the repetitive deformation that occurs in the mechanically dynamic environment in the bone defect site. As illustrated in Example 6 below, the hydrogel thus formed may have a compressive strength ranging from 300 kPa to 500 kPa, such as about 400 kPa, as measured by a texture analyzer. As commonly known in the art, the term "compressive strength" may refer to the value calculated from a load-deformation curve derived from a tensile test on a cured hydrogel, where a compression force of 5 kg is applied at a speed of 1.0 mm/second.

The hydrogel herein is also suitable for serving as a carrier for delivery of osteogenic substances. Therefore, the invention further contemplates a medical formulation which comprises the injectable hydrogel precursor composition herein in combination with an osteogenic substance. The term "osteogenic substance" as used herein may refer to a substance that can actively promote bone formation or ameliorate a condition which is thought to be unfavorable to bone formation. Examples of the osteogenic substances may include, but be not limited to, mesenchymal stem cells, stem cell secretomes, platelet-rich fibrins, platelet-rich plasma, chemotherapeutic drugs, growth factors, cytokines, antibiotics, and combinations thereof. The osteogenic substance can, if appropriate and desired, be lyophilized and stored in a sterile ampoule ready for reconstitution by addition of an aqueous medium, such as distilled water. In one preferred embodiment, the osteogenic substance comprises a platelet-rich fibrin (PRF), which is a platelet concentrate originated from autologous or donor blood obtained immediately after centrifugation through erythrocyte removal and is rich in growth factors, including transforming growth factor-beta (TGF-β), bone morphogenetic protein (BMP), insulin-like growth factor-1 (IGF-1), fibroblast growth factor (FGF), vascular endothelial growth factor (VEGF) and platelet derived growth factors (PDGFs). In another preferred embodiment, the osteogenic substance comprises an antibiotic for treating a patient afflicted with or at risk of a bacterial infection, such as vancomycin. Methods for combining the injectable hydrogel herein with the osteogenic substance are generally known in the art, which involve preparing the injectable hydrogel precursor composition as described above, following by adding the osteogenic substance to the composition and mixing thoroughly, until the osteogenic substance is evenly distributed in the composition. The obtained medical formulation is ready for injection to, for example, a segmental bone defect site, where it transitions to gel form. As described in Example 6 below, the mechanical strength of the hydrogel herein will not be reduced considerably by loading an osteogenic substance to the hydrogel.

As evidenced by Examples 7, 8 and 9 below, the hydrogel disclosed herein, either loaded with or without an osteogenic substance, is shown to exhibit low cytotoxicity and high biocompatibility in vitro and in vivo. From the experimental results shown in Examples 8 and 9, it can be appreciated that the hydrogel herein, either loaded with or without an osteogenic substance, exhibits suitable biodegradation kinetics in vitro and in vivo for serving as an orthopedic implant. It is further demonstrated in Example 10 below that such biodegradation kinetics advantageously result in timely release of the osteogenic substance from the hydrogel to promote bone formation.

The invention further contemplates the medical use of the formulation disclosed herein for treating a segmental bone defect, as well as a therapeutic method for treating a segmental bone defect in a patient, comprising administering to the patient the medical formulation disclosed herein. As used herein, the term "segmental bone defect" may refer to a partial or circumferential loss of bone tissues, which creates a defect site between a first bone end and a second bone end disconnected to the first bone end, and the bone marrow cavity at the defect site is completely exposed. Segmental bone defects can occur in various bones, which include but are not limited to femur, tibia, humerus, radius ulna, clavicle, and mandibular bones. In certain embodiments, the segmental bone defect is a critical segmental bone defect, which is defined herein as the minimum amount of bone loss that will not heal spontaneously by bone formation in the lifetime of a patient. Typically, a critical segmental bone defect has a >50% circumferential loss or a length of >2 cm in adult human patients.

The term "treating" or "treatment" includes providing structural support and/or promotion of bone formation at a bone defect site, reduction of the severity of a segmental bone defect, amelioration of one or more of the symptoms caused by a segmental bone defect, or deceleration or inhibition of the deterioration of a segmental bone defect.

Patients suitable for the treatment encompass human or non-human vertebrates, such as non-human mammals. Non-human mammals include livestock animals, companion animals, laboratory animals, and non-human primates. Non-human patients also include, without limitation, horses, cows, pigs, goats, dogs, cats, mice, rats, guinea pigs, gerbils, hamsters, mink, and rabbits. It is understood that the preferred patient is a human patient, especially a human patient suffering from a segmental bone defect.

The following examples are given for the purpose of illustration only and are not intended to limit the scope of the invention. Each experimental result is presented by mean±standard deviation. Statistical significance was considered when a p value of quantitative data is below 0.05. The imaging, histological, and biomechanical data were examined utilizing Student's t-test. The experimental groups labeled by asterisk (*) superscript letters, indicate that a statistical difference in the pair groups possessed the p value of <0.05, and was deemed as statistical significance.

Example 1: Preparation of Genipin Crosslinked-Gelatin/Hyaluronic Acid Hydrogels 10 wt % gelatin (type B, average molar mass: 40,000-50,000 g/mol, Sigma-Aldrich®, USA) and 1 wt % hyaluronic acid (mass-average molecular weight: 8000-10,000 kDa, Foodchemifa Co., Ltd., Japan) were suspended in deionized water to obtain a GLT/HA blend. The blend was aliquoted into five equal parts, to which different amounts of genipin (molar mass: 226.2 g/mol, Challenge Bioproducts Co., Ltd., Taiwan) were added to reach final concentrations of 0.025 wt %, 0.05 wt %, 0.1 wt %, 0.5 wt % and 1.0 wt %, respectively. The obtained mixtures were cured into GP crosslinked-GLT/HA hydrogels by stirring at 300 rpm at 37° C., during which the respective mixtures were characterized in the following examples.

Example 2: Preparation of Lyophilized Platelet-Rich Fibrin 8 mL of rabbit venous blood was drawn from jugular vein and collected into a sterilized-tube without anti-coagulant supplement (Vacuette 455071, Greiner Bio-one, Austria). The coagulation cascade was activated by the micronized silica particles coated on the inner wall of the tube. The tubes were then centrifuged for 5 minutes at 400×g within a centrifuge (DSC-200A-2 tabletop, Digisystem, Laboratory Instruments, New Taipei City, Taiwan). After centrifugation, a layer of platelet-rich fibrin (PRF) was formed between an upper layer of acellular plasma and a lower layer of red blood cells. For preparation of lyophilized PRF (LPRF), fresh PRF was first frozen and stored at −80° C. for 24 hours, and the frozen PRF was then lyophilized overnight using a Freeze Dryer System (KingMech Scientific Co., LTD., New Taipei City, Taiwan) at −51° C. The LPRF was ground into powder for subsequent use.

Example 3: Preparation of Hydrogels Loaded with PRF

Example 1 was repeated to prepare colloidal suspensions of GLT/HA hydrogel containing 0.5 wt % GP (referred to as GLT/HA-0.5% GP hereafter), to which 25 mg and 50 mg of LPRF powder prepared in Example 2 were added, respectively. The hydrogel suspensions were continuously stirred under magnetic stirring at 37° C. until powder was fully dissolved. The LPRF-loaded hydrogels thus obtained were referred to hereafter as GLT/HA-0.5% GP hydrogel loaded with 25 mg and 50 mg of LPRF, respectively.

FIG. 1 shows scan electron microscopic images of the GLT/HA-0.5% GP hydrogel formed from the composition prepared in Example 1 and the two LPRF-loaded hydrogels formed from the compositions prepared in Example 3. The LPRF-loaded hydrogels have a similar microstructure to GLT/HA-0.5% GP hydrogel, indicating that they share a similar porous structure with a similar pore size distribution. Moreover, a honeycomb-like porous morphology with interconnected pores was observed in those hydrogels. The open porosity of the scaffold will function to support the cellular on/ingrowth of osteoblasts and bone mineralization.

Example 4: Rheological Property and Gelation Time

Rheological properties of the GLT/HA-0.5% GP hydrogel prepared in Example 1, the LPRF-loaded hydrogels prepared in Example 3 and the non-crosslinked GLT/HA hydrogel were measured using a parallel-plate rheometer (AR2000ex, TA Instruments, New Castle, DE, USA). A time sweep at 1 Hz of the GLT/HA, GLT/HA-0.5% GP and GLT/HA-0.5% GP hydrogels loaded with 25 or 50 mg of LPRF were evaluated by placing the test samples within the plates and continuously recording the storage moduli (G') and loss moduli (G") at 37° C.

Figure 2:
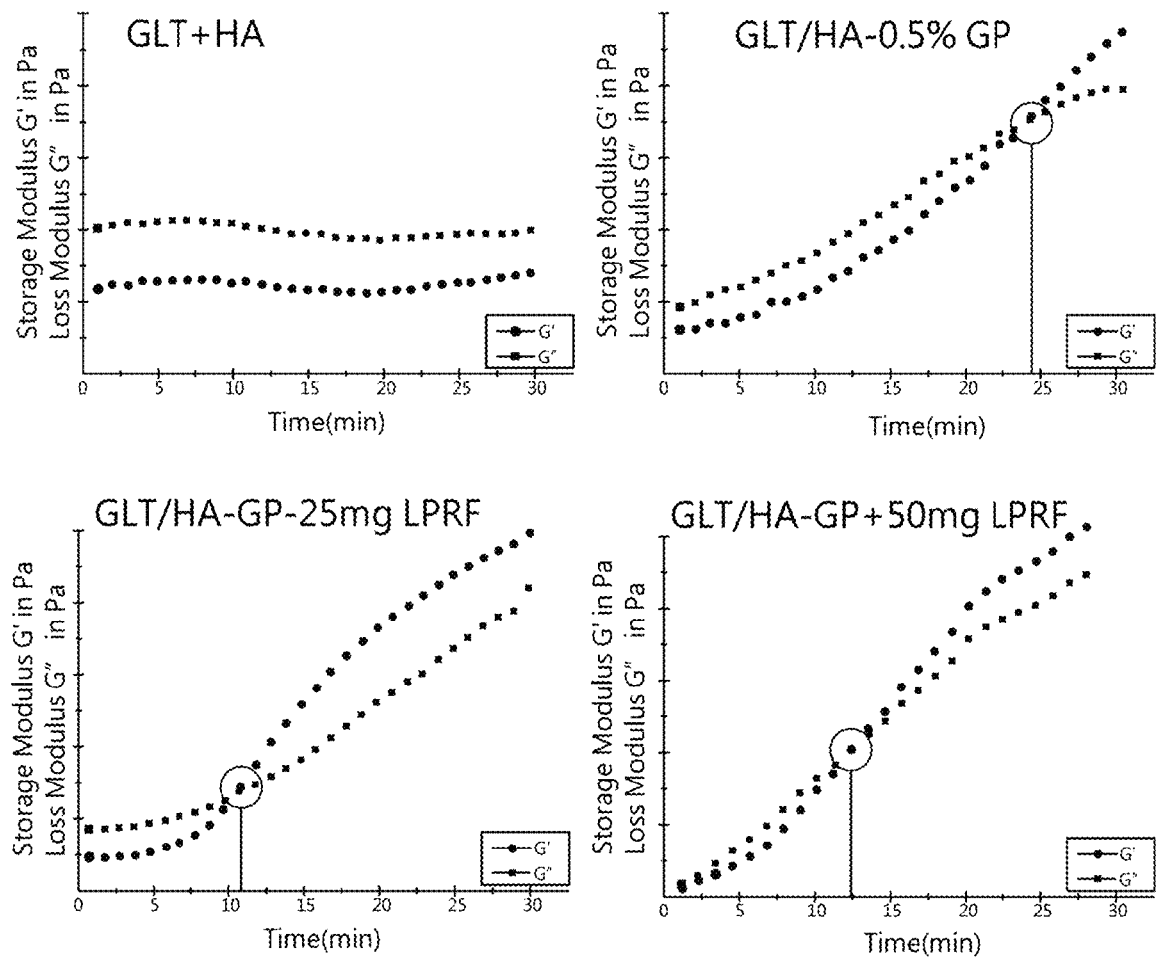
FIG. 2 shows rheological property of the hydrogels according to the invention.

As shown in FIG. 2, the storage moduli (G') and loss modulus (G") of GLT/HA-0.5% GP was constantly higher than those of GLT/HA-GP with a crossover point of G' and G" of about 23 minutes, indicating that GLT/HA-0.5% GP was stably crosslinked in the presence of GP and had a gelation time of about 23 minutes. Meanwhile, GLT/HA-0.5% GP hydrogels loaded with 25 or 50 mg of LPRF had crossover points of G' and G" of about 12 and 15 minutes, respectively, and the average values of G' and G" for the LPRF-loaded hydrogels were higher than those of GLT/HA-0.5% GP, indicating that mechanical strength increased with incorporation with PRF into GLT/HA-0.5% GP.

Example 5: Syringteability of Hydrogels

To simulate the working conditions and time frame for a segmental bone defect surgery, which require that a hydrogel precursor composition have sufficient flowability at room temperature before being applied to a bone defect site through an injection device, the hydrogels prepared in Example 1 were tested for syringeability at 25° C. In the test, each hydrogel was loaded into a 3 mL syringe with 21 G needle (30×0.8 mm in diameter), and the syringeability was measured at 0 minute, 15 minutes and 60 minutes post loading, in terms of the residual mass of the hydrogel retained in the syringe by applying manual force for 5 seconds.

The bottle inversion test was further used to measure the solution-gelation transition times of the hydrogels prepared in Examples 1 at physiological temperature. The test was initiated at T0, when the hydrogels prepared in Example 1 were placed in capped bottles, respectively, and allowed to stand for 1 minute. The flowabilities of the respective mixtures at T10 (10 minutes from T0), T20 (20 minutes from T0) and T30 (30 minutes from T0) at 37° C. were determined by tilting the respective bottles upside-down, and the gelation times were determined when the mixtures stop flowing.

Figure 3A:
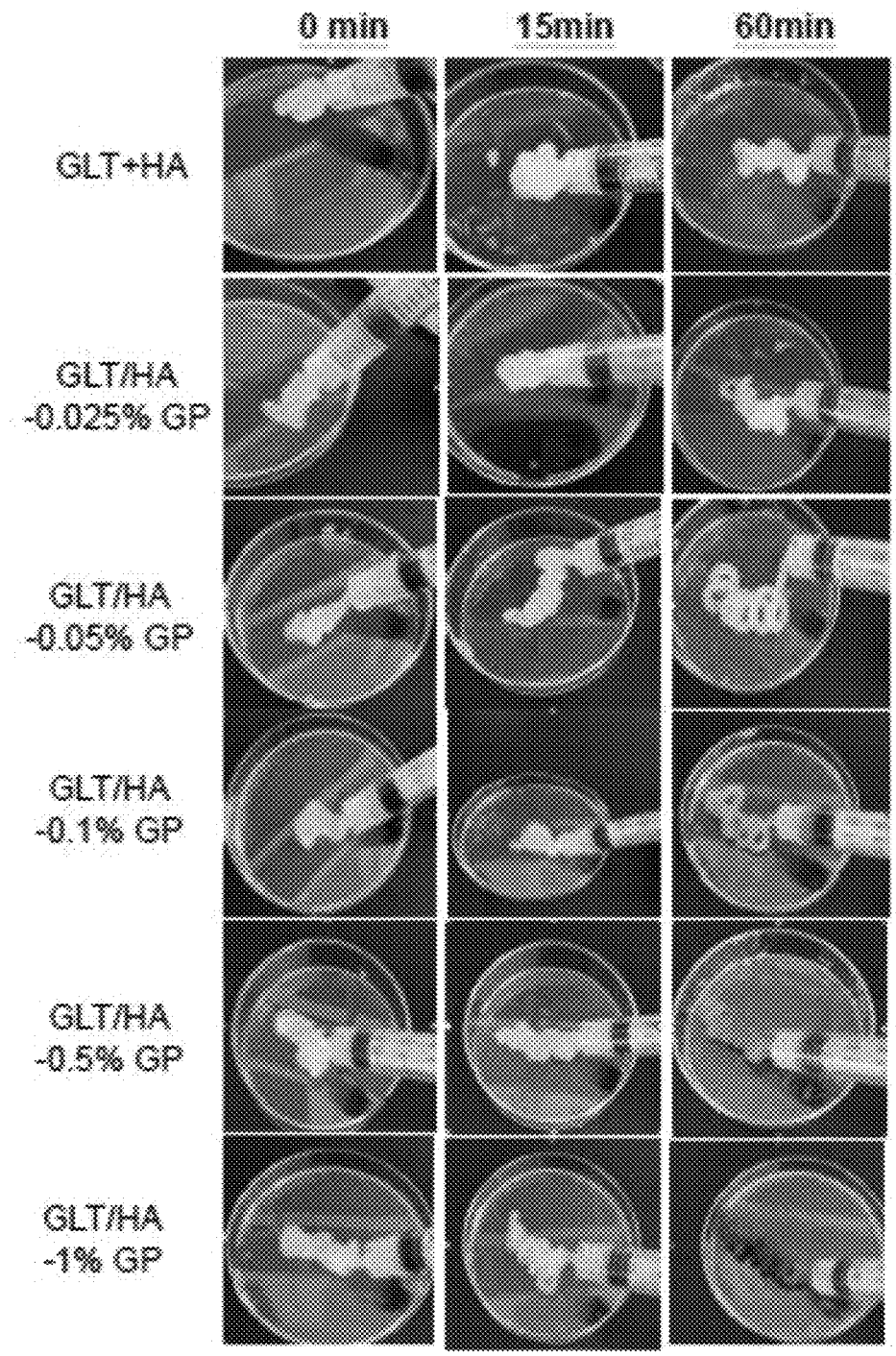
FIG. 3A shows the injectability of the hydrogels according to the invention at ambient temperature.
Figure 3B:
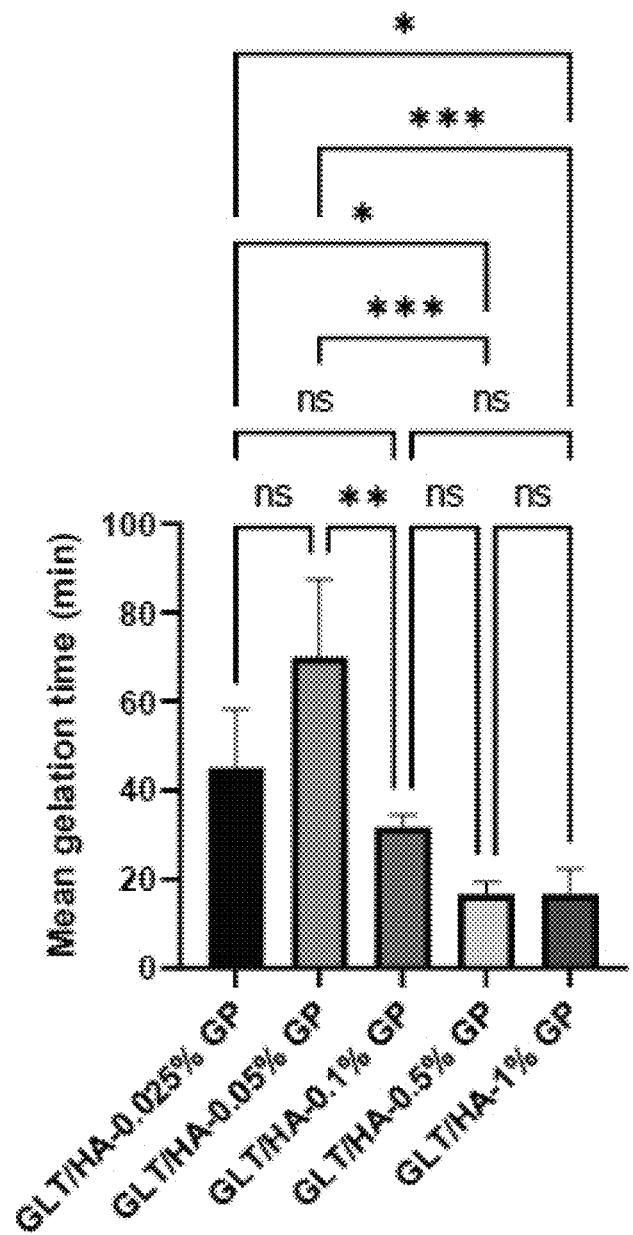
FIG. 3B is a histogram showing the mean gelation time of the hydrogels according to the invention at physiological temperature.

As shown in FIGS. 3A and 3B, the thermoresponsive behaviors of the hydrogels prepared in Example 1 are related to the degree of GP crosslinking. Specifically, GLT/HA-0.025% GP and −0.05% GP hydrogels were shown injectable at ambient temperature even after 24 hours post-formulation. At 37° C., the two hydrogels gradually gelled and formed stable construct after 40 minutes as demonstrated by the bottle inversion test. In comparison, GLT/HA-0.5% GP and −1% GP hydrogels exhibited relatively rapid gelation time of about 20-25 minutes at 37° C., which is consistent with the values obtained by using a rheometer as shown in Example 4 above, while remaining injectable for at least 60 minutes at ambient temperature. In overall, the gelation times of the hydrogels decreased from 37.5 minutes to 29, 26.5, 25, and 20.5 minutes at 37° C. when GP concentration gradually increased from 0.025% to 0.05%, 0.1%, 0.5% and 1%, respectively.

Example 6: Mechanical Property of Hydrogels

After transitioning to gel state, the hydrogels prepared in Example 1, the LPRF-loaded hydrogels prepared in Example 3, and the non-crosslinked GLT/HA hydrogel were tested for mechanical property using a texture analyzer (model TA.XT Plus, Texture Technologies Corp., Scarsdale, NY, USA) at ambient temperature with a cylinder probe of SMS P/25 to compress the samples. Plate samples (1 cm³ in size) were subjected to a tensile test using a 5 kg load cell at a test speed of 1.0 mm/sec. The individual tensile modulus and fracture strength were obtained from the stress-strain curve, where $\Delta\sigma$ is the stress (N/mm$^2$) and $\Delta\varepsilon$ is the strain (mm/mm) under tensile measurement. All of the hydrogels were tested in triplicate for each group.

Figure 4A:
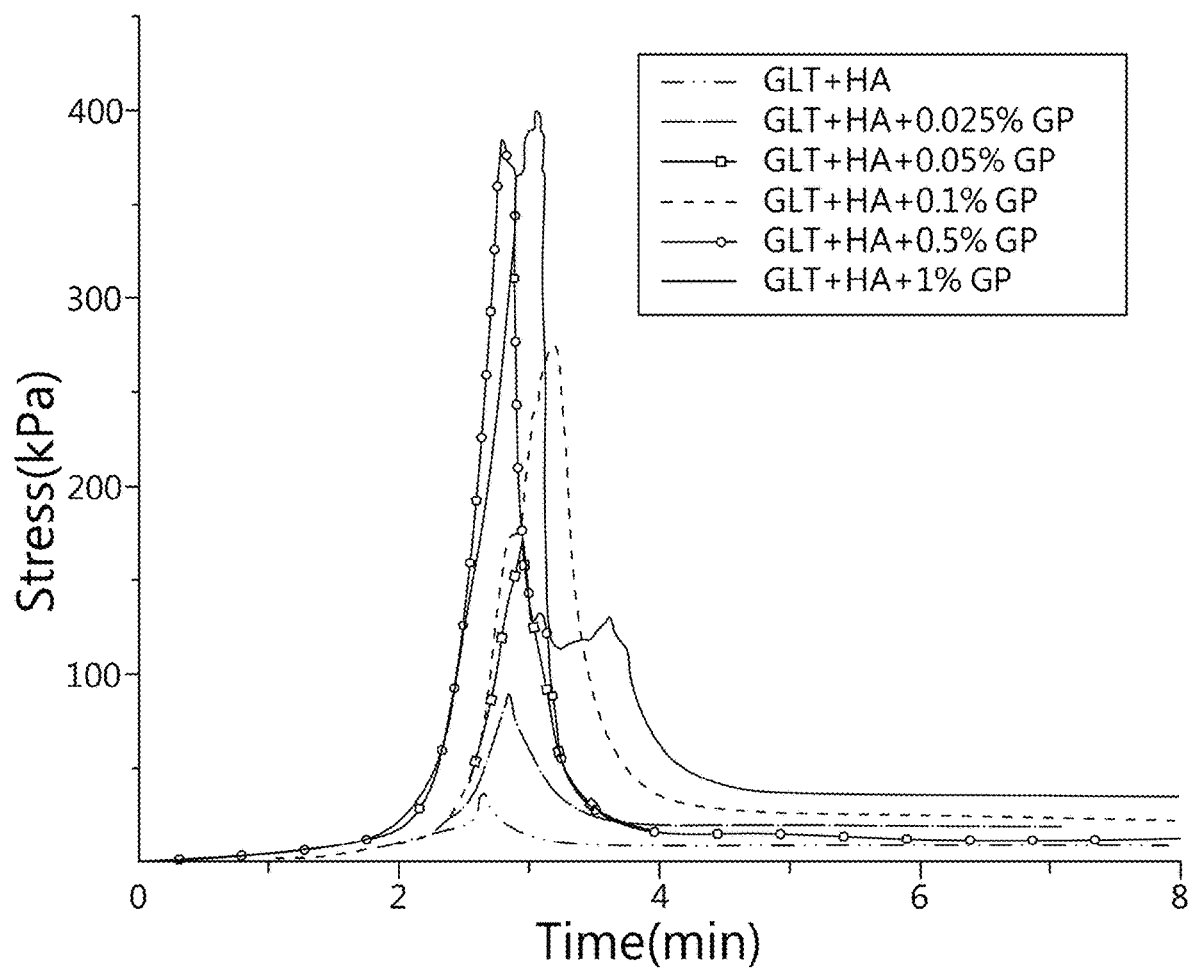
FIG. 4A shows the mechanical property of the hydrogels according to the invention.
Figure 4B:
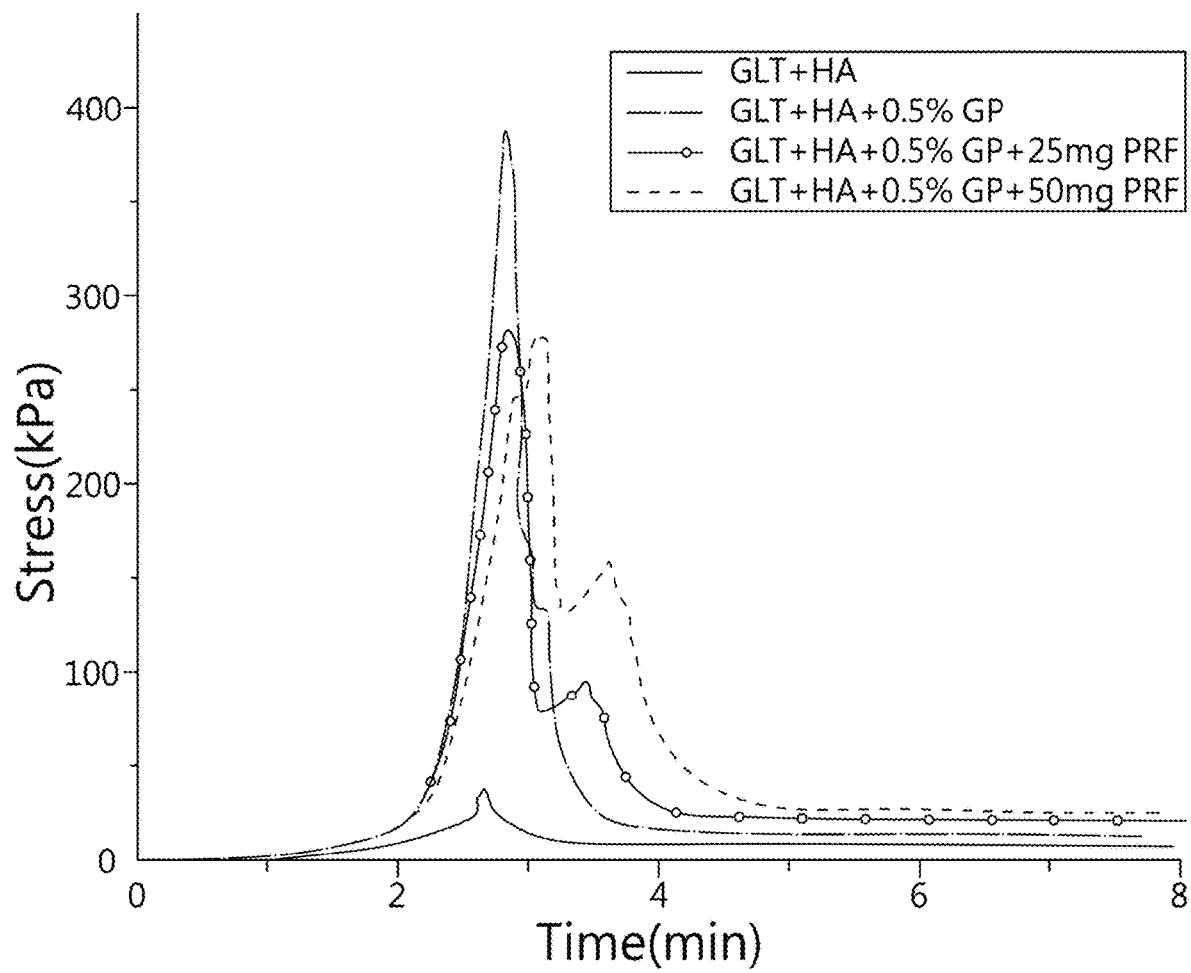
FIG. 4B shows the mechanical property of the hydrogels loaded with or without platelet-rich fibrin.

As shown in FIG. 4A, the non-crosslinked GLT/HA hydrogel exhibited a poor mechanical strength of less than 50 kPa, rendering it unsuitable for use in bone tissue engineering applications. In contrast, the mechanical strengths of the GLT/HA hydrogels prepared in Example 1 increased with the increasing of the GP concentration, indicating that the mechanical property of the hydrogel herein can be tuned by adjusting the extent of GP crosslinking. When GP was added in an amount from 0.5 wt % to 1.0 wt %, the hydrogels herein exhibited a compressive strength of about 400 kPa. FIG. 4B further shows that the GP-crosslinked hydrogels, including GLT/HA-0.5% GP hydrogel and the LPRF-loaded hydrogels, were able to withstand compressive stress of hundreds kPa without breaking down or collapsing. Specifically, the LPRF-loaded hydrogels had a compressive strength of about 275 kPa, suggesting that the loading of LPRF did not considerably interfere with the structural integrity or impair the mechanical strength of the composite hydrogels.

Example 7: Cytotoxicity and Biocompatibility

In vitro biocompatibility of the hydrogels formed from the compositions prepared in Example 1, the LPRF-loaded hydrogels formed from the compositions prepared in Example 3, and the non-crosslinked GLT/HA hydrogel were evaluated according to the ISO 10993-5:2009 standard. 1 $cm^3$ cubic-shaped samples were divided from the respective hydrogels and immersed in Dulbecco's Modified Eagle's Medium (DMEM) (Gibco, Invitrogen Taiwan Ltd., MD) for 24 hours, respectively, and the supernatants were collected afterwards. L929 fibroblast cells (purchased from National Institute of Health, Taiwan) were seeded in a 96-well microplate at a density of $1 \times 10^3$ cells per well in DMEM supplemented with 10% fetal bovine serum (FBS) (Gibco®, Grand Island, NY, USA) and allowed to attach overnight. The DMEM was removed, and the supernatants were added to the cell culture. After a 24-hour incubation, the viable cell number in each well was counted with thiazolyl blue tetrazolium bromide (MTT; Sigma-Aldrich, Saint Louis, MO, USA). The absorbance of each solution was measured at a wavelength of 595 nm with a microplate reader (Bio-Rad) in quadruplicate.

For measuring the amounts of reactive oxygen species (ROS) generated by the respective hydrogels, L929 cells were treated with the supernatants derived from the hydrogels for 24, 48 and 72 hours, respectively, and then washed and stained by hydroethidine (HE). Cells were harvested and analyzed with flow cytometry afterwards.

Figure 5:
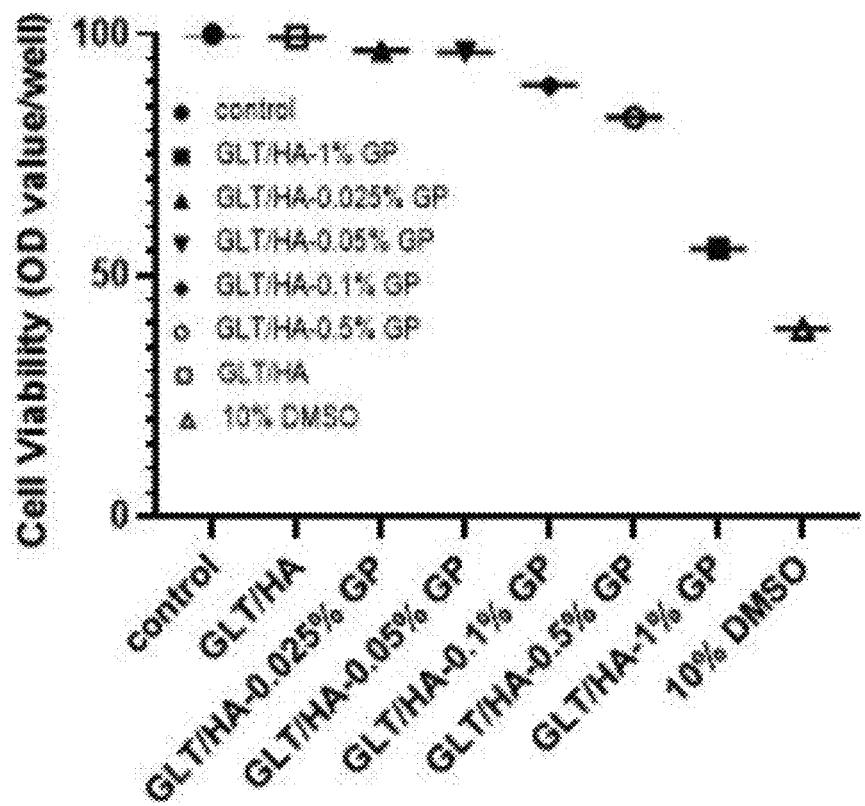
FIG. 5 shows the cytotoxicity of the hydrogels crosslinked by genipin according to the invention.
Figure 6:
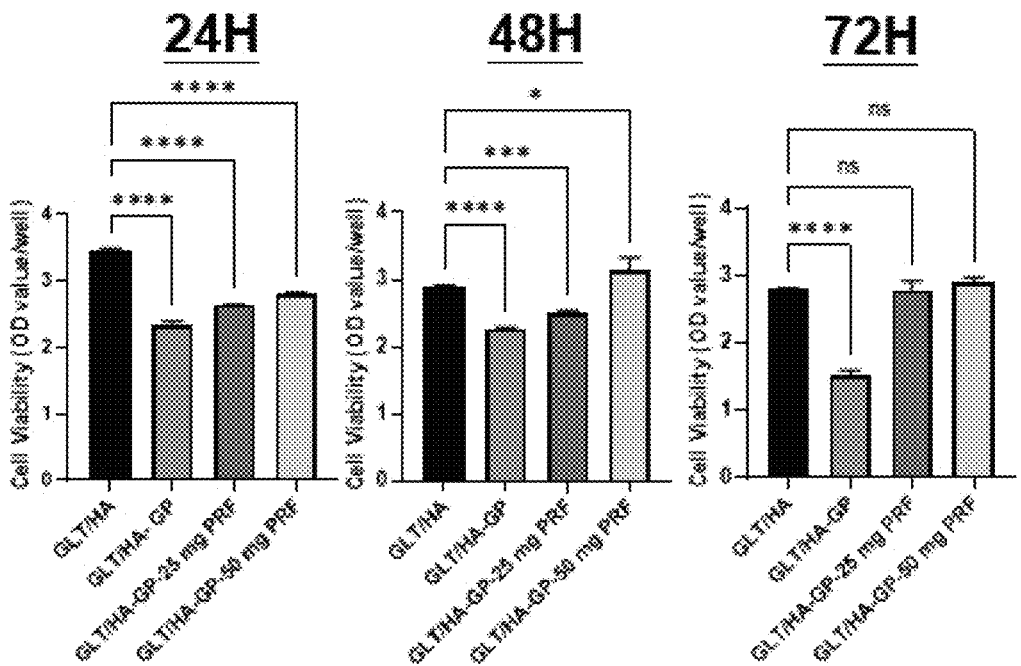
FIG. 6 is a histogram showing the cytotoxicity of the hydrogels over time.
Figure 7:
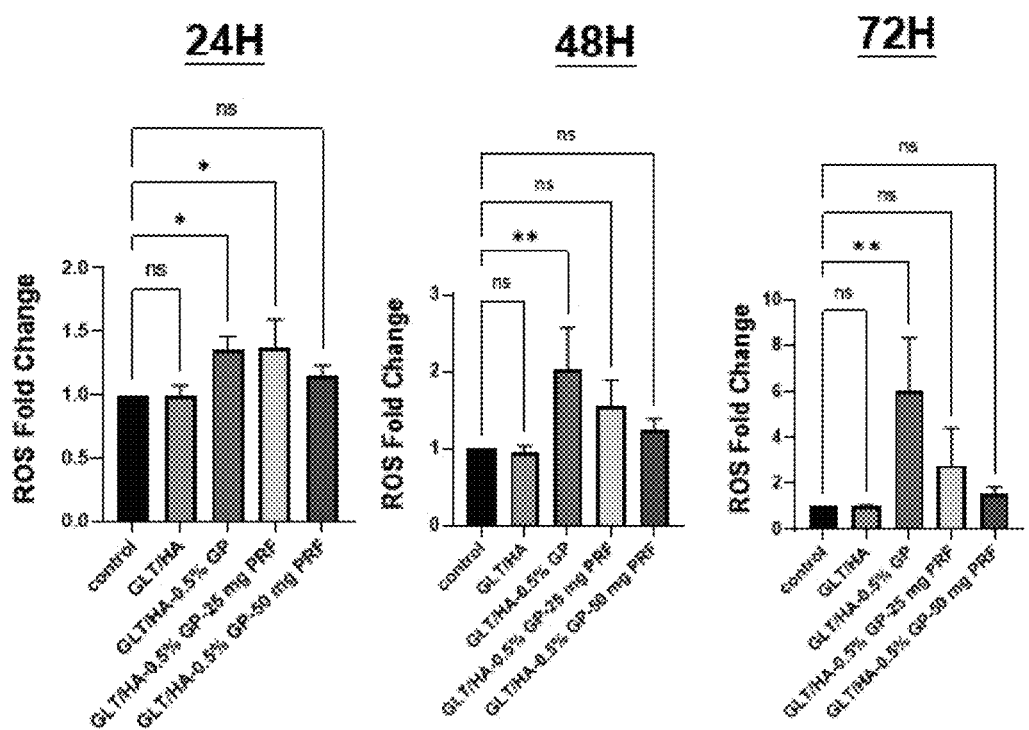
FIG. 7 is a histogram showing the ROS fold change of the hydrogels over time.

As shown in FIG. 5, while the cytotoxicity of the hydrogels was directly proportional to the increased concentration of GP, all of the hydrogels prepared in Example 1, including those having GP concentration from 0.5 wt % to 1.0 wt %, did not exhibit considerable cytotoxicity to cells. Although the results of the MTT assay shown in FIG. 6 indicate that cell viability in GLT/HA-0.5% GP hydrogel decreased steadily from $24^{th}$ hour to $48^{th}$ hour and further dropped at $72^{nd}$ hour post-seeding, such negative outcome can be countered in a dose-dependent manner by loading LPRF to the hydrogel, as shown in FIGS. 6 and 7.

Example 8: In Vitro Biodegradation

The in vitro biodegradation features of the GLT/HA-0.5% GP hydrogel prepared in Example 1, the LPRF-loaded hydrogels prepared in Example 3 and the non-crosslinked GLT/HA hydrogel were evaluated by first measured the initial weight of 1 $cm^3$ cube-shaped hydrogels in each group. Subsequently, the hydrogels were incubated at 37° C. in 3 mL of PBS buffer with gentle agitation in an orbital shaker. At each time point (0 hour, $12^{nd}$ hour, $24^{th}$ hour, $48^{th}$ hour, $72^{nd}$ hour, Day 6, Day 9, Day 12), the hydrogels were taken from the medium, blotting with a filter paper, and finally weighed accordingly. After that, the medium was replaced with fresh PBS. Percentage of weight loss was plotted against the degradation time.

Figure 8:
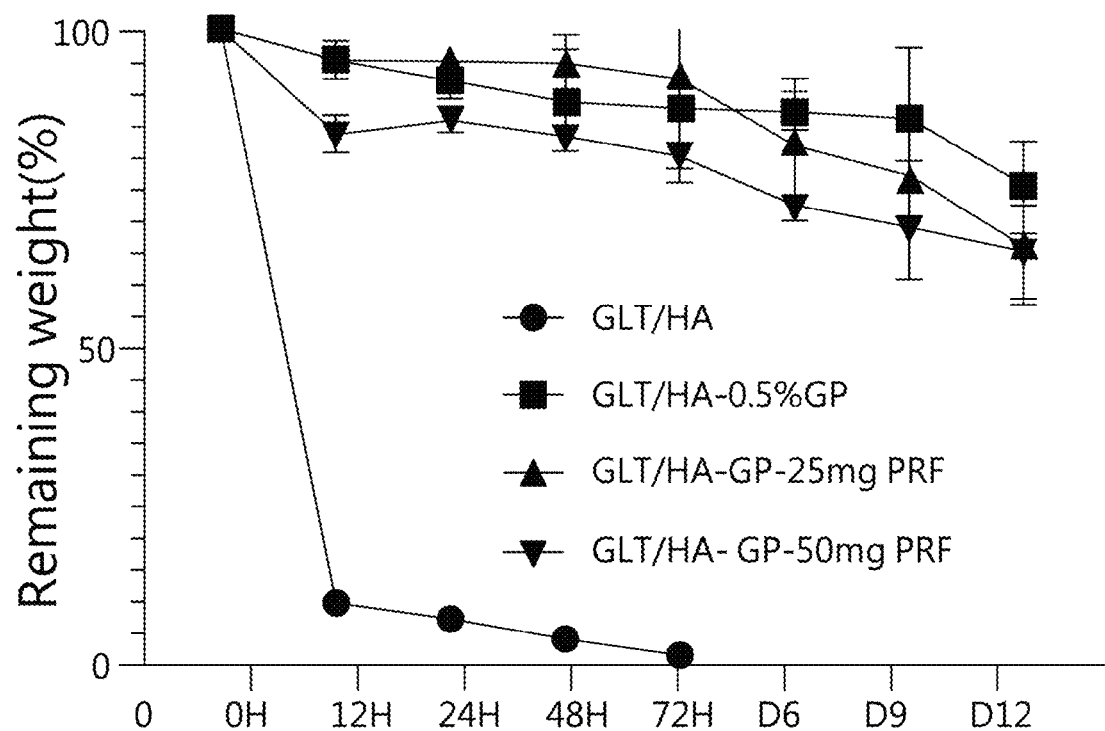
FIG. 8 shows the in vitro biodegradation rates of the hydrogels loaded with or without platelet-rich fibrin.

As shown in FIG. 8, the biodegradation rates of the hydrogels tested decreased with addition of either GP or GP plus LPRF, suggesting that the addition of GP and LPRF slowed down the biodegradation rate of the hydrogels. The data reveal that the LPRF-loaded hydrogels herein exhibit desirable biodegradation performance for further in vivo applications as an orthopedic implant.

Example 9: In Vivo Subcutaneous Hydrogel Implantation

All animal experiments were approved by the Institutional Animal Care and Use Committee. Food and water were provided ad libitum. Ten male ICR mice (weighing from 20 to 25 g) were anesthetized using 2-2.5% isoflurane in oxygen at 1.5-2 L/min. In vivo biocompatibility and biodegradability were analyzed by implanting hydrogels subcutaneously onto the back of mice. Briefly, two subcutaneous pockets were created, and hydrogel samples (GLT/HA, GLT/HA-0.5% GP or GLT/HA/0.5% GP-50 mg LPRF) were implanted in these pockets separately and subjected to degradation over a 28-day period. On day 0, 7, 14, 21, 24, and 28, magnetic resonance images were taken.

Figure 9:
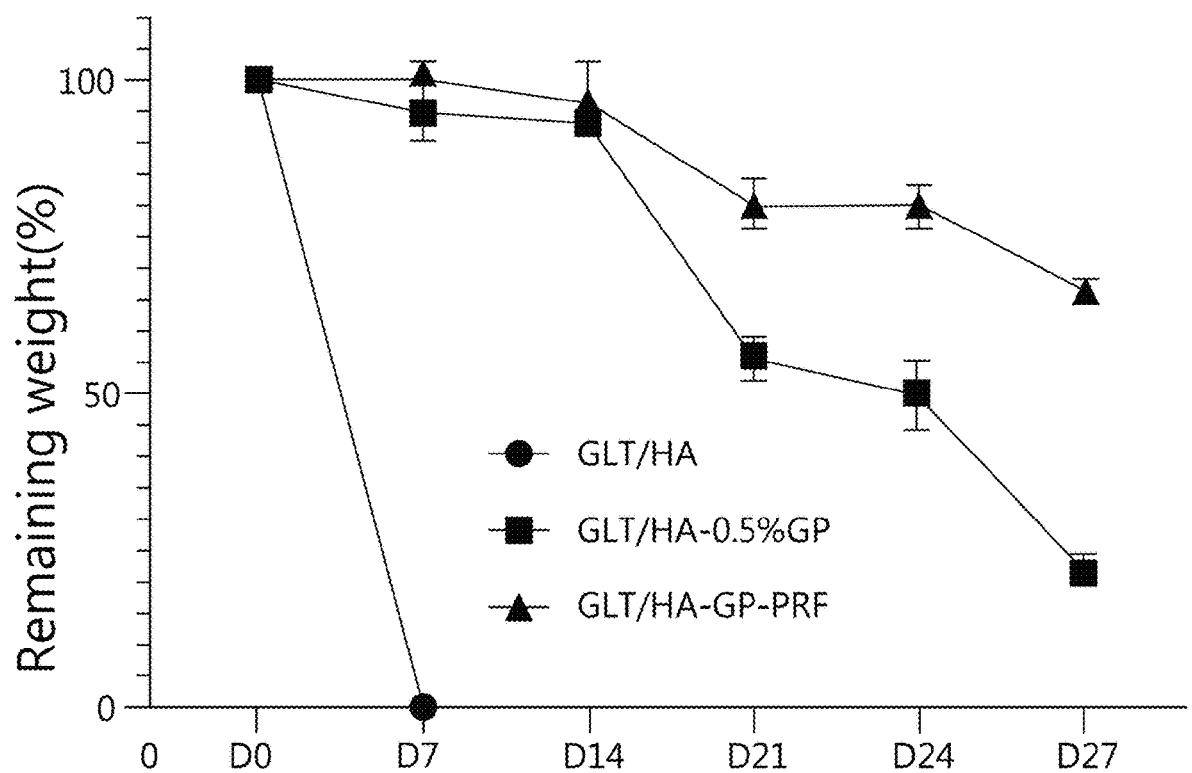
FIG. 9 shows the in vivo biodegradation rates of the hydrogels loaded with or without platelet-rich fibrin.
Figure 10:
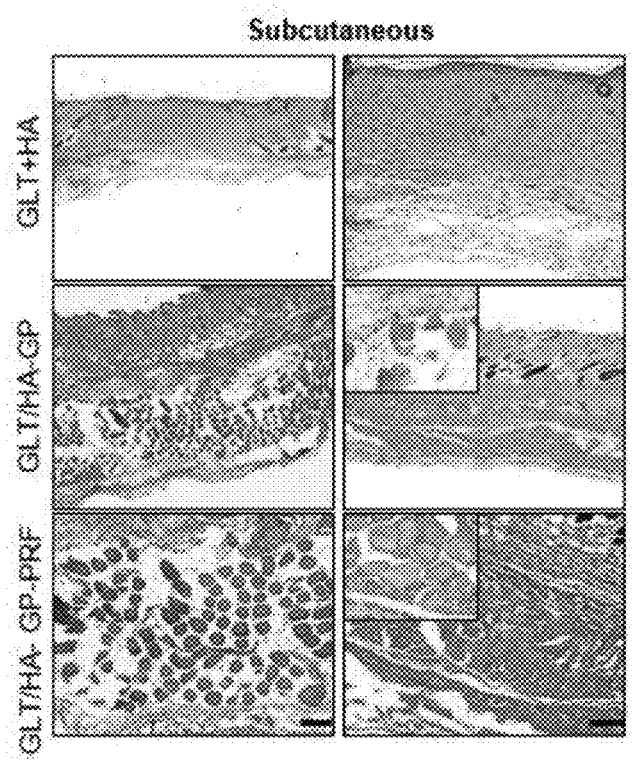
FIG. 10 is histological images showing the mouse subcutaneous tissues implanted with the hydrogels according to the invention.
Figure 11:
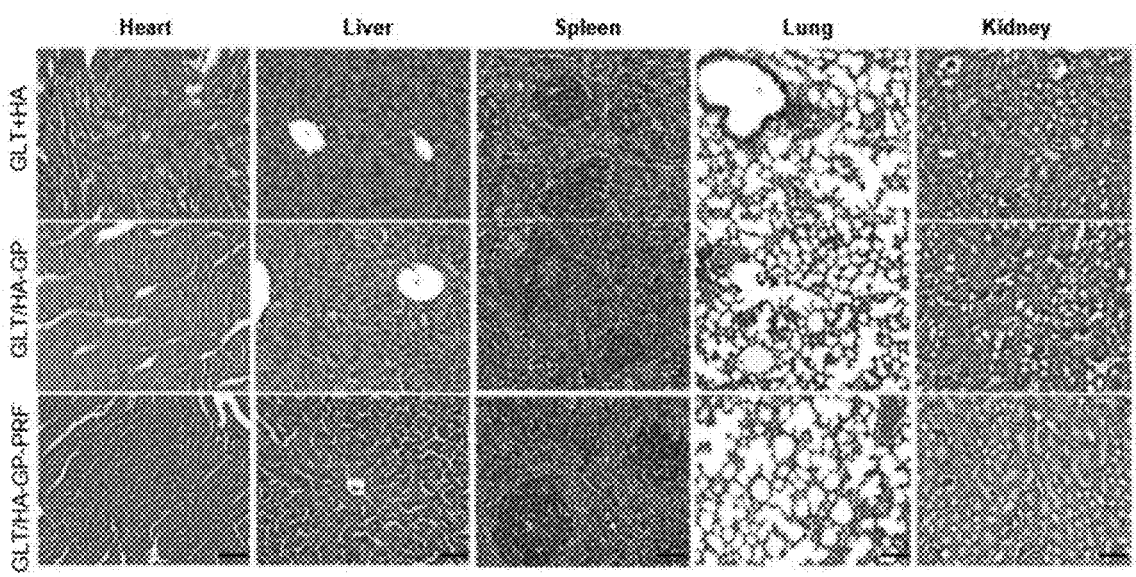
FIG. 11 is histological images showing the systemic toxicity of the implanted hydrogels to vital visceral organs.
Figure 12:
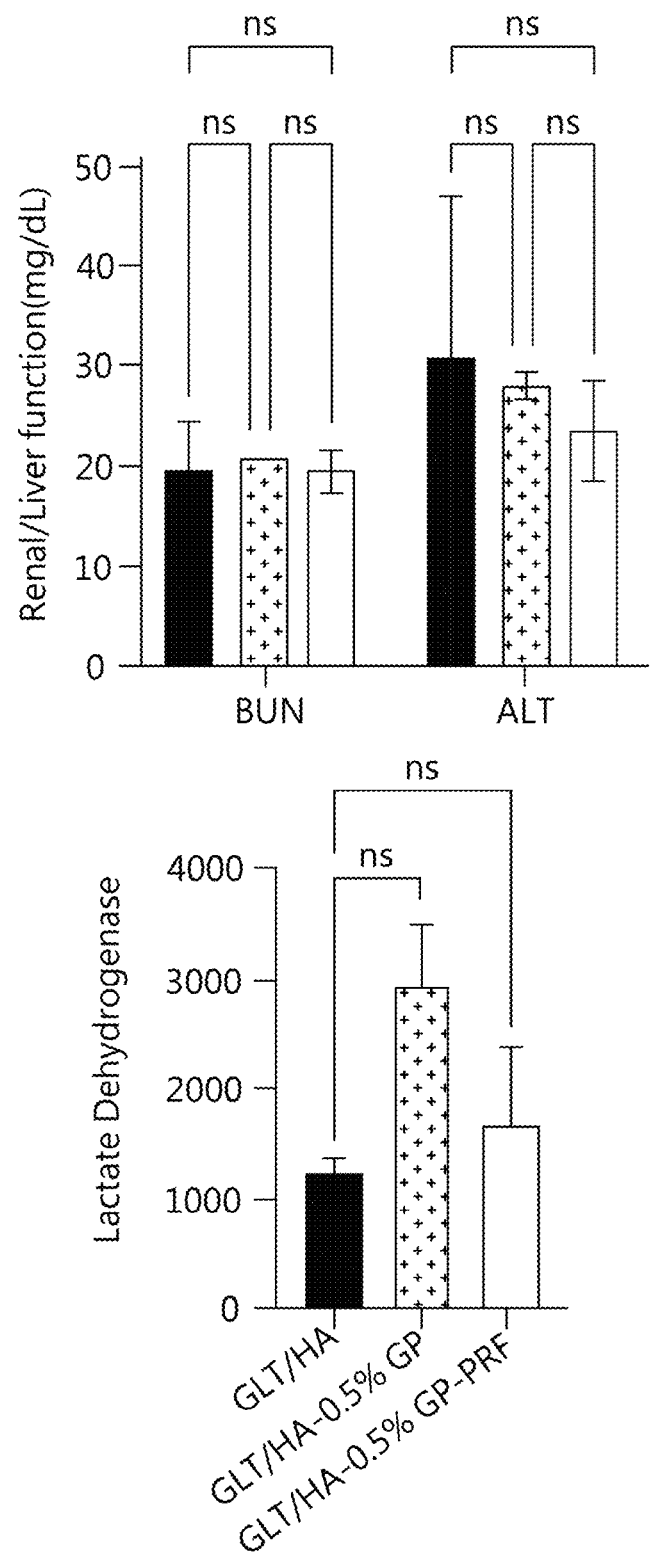
FIG. 12 is a histogram showing the serum levels of renal (BUN), liver (ALT) and proinflammatory marker (LDH) of the mice implanted with the hydrogels according to the invention.

The remaining volume analysis shown in FIG. 9 indicates that the sizes of GLT/HA-GP and GLT/HA-GP-LPRF hydrogels gradually decreased in the first 14 days. Histological analysis of the subcutaneous tissues implanted with hydrogels shows that these hydrogels were encapsulated by thin fibrous tissues but without notable inflammatory cells aggregation (FIG. 10). The systemic toxicity (e.g., hyperemia, edema, necrosis) of the implanted hydrogels to vital visceral organs including heart, liver, spleen, lung and kidney was not detected either (FIG. 11). To further investigate the systemic reaction after hydrogel implantation, the serum levels of renal (BUN), liver (ALT), and proinflammatory marker (LDH) were measured in all three groups of mice implanted with different hydrogels. Serum of animals implanted with non-crosslinked GLT/HA serves as control. The results show that all three groups of animals displayed normal renal and liver functions. No significant difference in serum LDH levels among the mice implanted with these hydrogels (FIG. 12).

Example 10: Rabbit Segmental Bone Defect Model

Eighteen skeletally mature New Zealand white rabbits (males, with a mean body weight of 2-2.5 kg) were used in this Example and divided into three groups. All animals were anesthetized with isoflurane and kept in a supine position, and the left limb was disinfected with povidone-iodine. An incision (6 cm) was made on the lateral aspect of the left limb to expose the tibia. Next, an oscillating saw was utilized to create a 10×5-mm defect in the lateral aspect of the tibia. In group A, the defect in vivo was left untreated which served as control (sham); in group B, the defect in vivo was implanted with GLT/HA-0.5% GP hydrogel; and in group C, the defect in vivo was implanted with GLT/HA- 0.5% GP-LPRF hydrogel. An 8-hole mini plate (VariAx Hand, Stryker) was applied laterally for fixation.

The treated wound was ultimately closed by an absorbable suture. Penicillin (2.2 mg/kg for 3 days) and ketoprofen (40,000 IU/kg for 3 days) were administered postoperatively for preventing infection of wound and controlling pain in treated animals. Animals were permitted to move in the animal cage without constraint.

Figure 13:
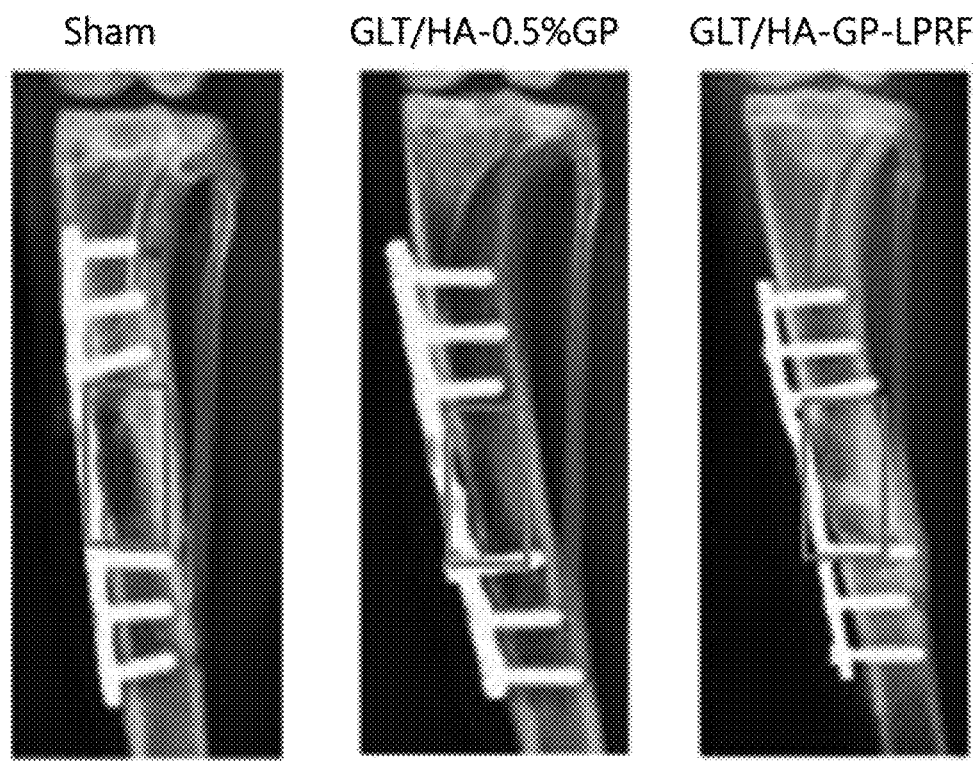
FIG. 13 shows radiographic images of rabbit tibia implanted with the hydrogels according to the invention.
Figure 14:
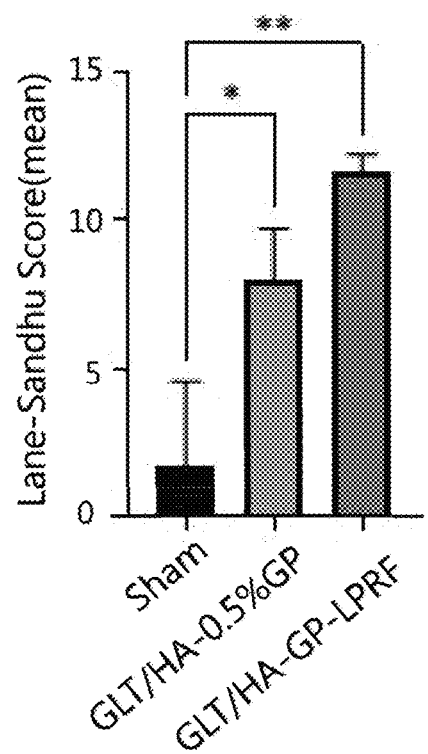
FIG. 14 is a histogram showing the Lane-Sandhu scores of rabbit tibia implanted with the hydrogels according to the invention.

To evaluate the bone healing among experimental groups, anteroposterior and lateral radiographic data of the left tibias of rabbits were taken at 8 weeks after the operation. For a quantitative assessment, digital radiographic images were scored according to the Lane-Sandhu scoring system. As shown in FIG. 13, radiographic analysis of the control group shows no or negligible bone formation at the non-implanted tibial defect, which is indicative of nonunion of segmental bone defect. Partial gap bridging of the defect was found in GLT/HA-GP group with limited amount of callus formed at the defect site. In all of the defects implanted with GLT/HA-GP-LPRF hydrogel, significant callus formation was detected, and nearly complete tibial defect bony bridging had occurred after treatment. Quantitatively, the Lane-Sandhu score for the GLT/HA-GP and GLT/HA-GP-LPRF groups were significantly higher than that for the control, as shown in FIG. 14.

Animals were sacrificed in anesthesia at 8 weeks' post-surgical process through an intra-muscular administration of xylazine hydrochloride (10 mg/kg, Bayer, Leverkusen, Germany) subsequently carbon dioxide (inhalation treatment). The whole tibia from animal were subsequently harvested.

Figure 15:
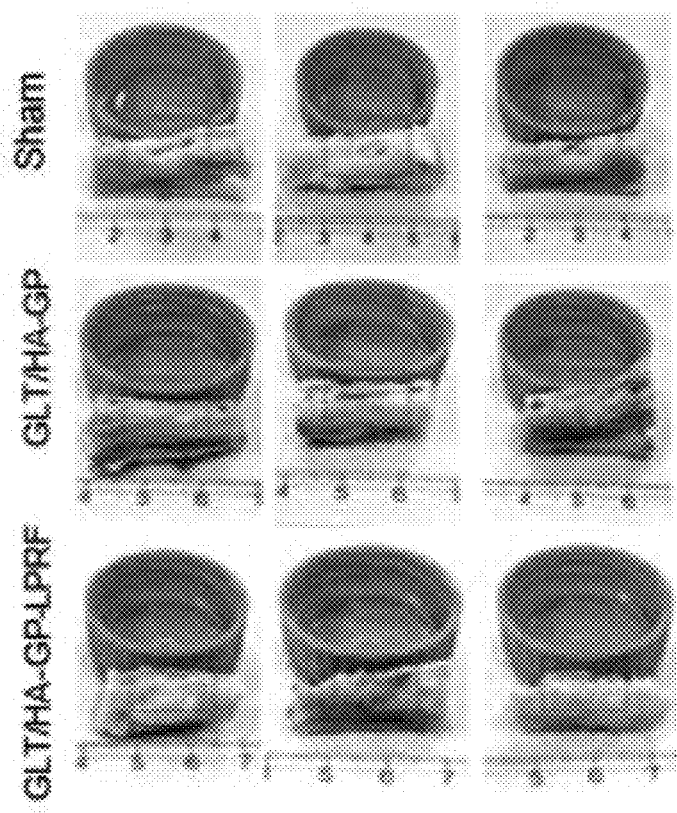
FIG. 15 shows macroscopic images of rabbit tibia implanted with the hydrogels according to the invention.

After the fixation implants were removed, the tibial defect region in each tibia was identified through visual observation of the relative position between the third and fourth screw holes. FIG. 15 shows macroscopic assessment of the tibia harvested. More new bone regeneration and better bone defect repair were observed visually in the rabbit groups implanted with GLT/HA-0.5% GP-LPRF hydrogel than in GLT/HA-0.5% GP and control hydrogels. In the rabbit group implanted with GLT/HA-0.5% GP-LPRF hydrogel, the defects were filled with reparative tissues, and the bony cortical surface was mostly continuous. In contrast, the untreated control showed very limited repair in the defect area, leaving a remarkable central depression on the bony surface. In GLT/HA-0.5% GP group, partial union of bony defect was noted.

Rabbit tibias were scanned by micro-CT (Skyscan 1176; Bruker, Billerica, MA, USA). Micro-CT scanning of the femurs was done at 90 kV, 8000×8000 pixels/slice, and a resolution of 35 μm. Once scanning, the micro-CT images were reconstructed to produce a 3D volume rendering using reconstruction software (NRecon Reconstruction; Bruker). The tibial defect area was selected by identifying the relative position between the third and fourth screw holes and was denoted as the region of interest (ROI). Images of new bone formation in the ROI were captured and analyzed. Microstructural measurements included bone volume (BV, mm3), the percentage of bone volume versus total tissue volume (BV/TV, %), bone thickness (mm), bone separation (mm), bone surface (mm), and bone surface/total tissue volume (1/mm).

Figure 16:
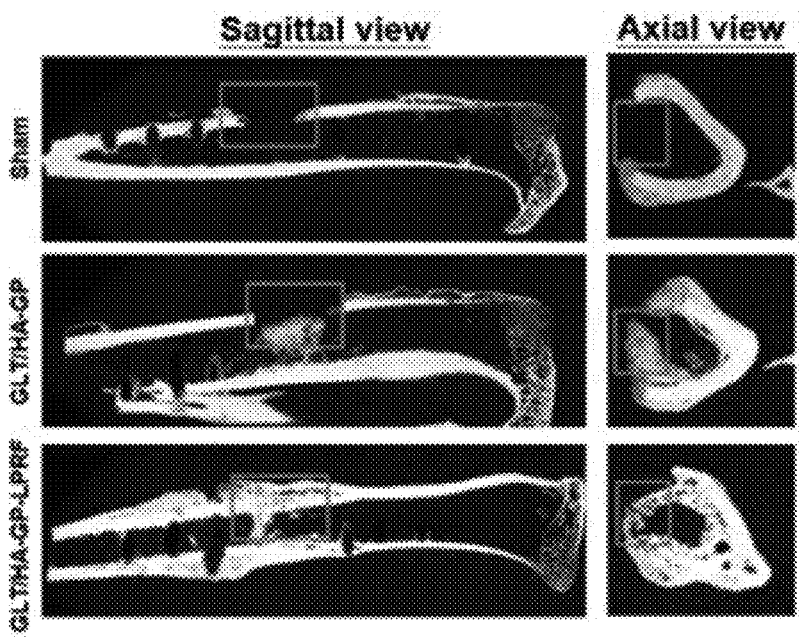
FIG. 16 shows micro-CT images of rabbit tibia implanted with the hydrogels according to the invention.

Through micro-CT imaging, new bone regeneration at the tibial segmental defect sites was demonstrated in different dimensions, including axial, sagittal and 3D reconstructed views. The results show that the defect gap in sham control group was observed with tiny quantity of new bone formation, indicative of bony nonunion after surgery. In addition, a central depression region could be clearly seen on tibias in control group as shown by 3D reconstructed images. In GLT/HA-GP group, although the tibial defects were partially filled with newly regenerated tissues, the cortical discontinuity largely remained, both on axial and sagittal views (FIG. 16).

Figure 17:
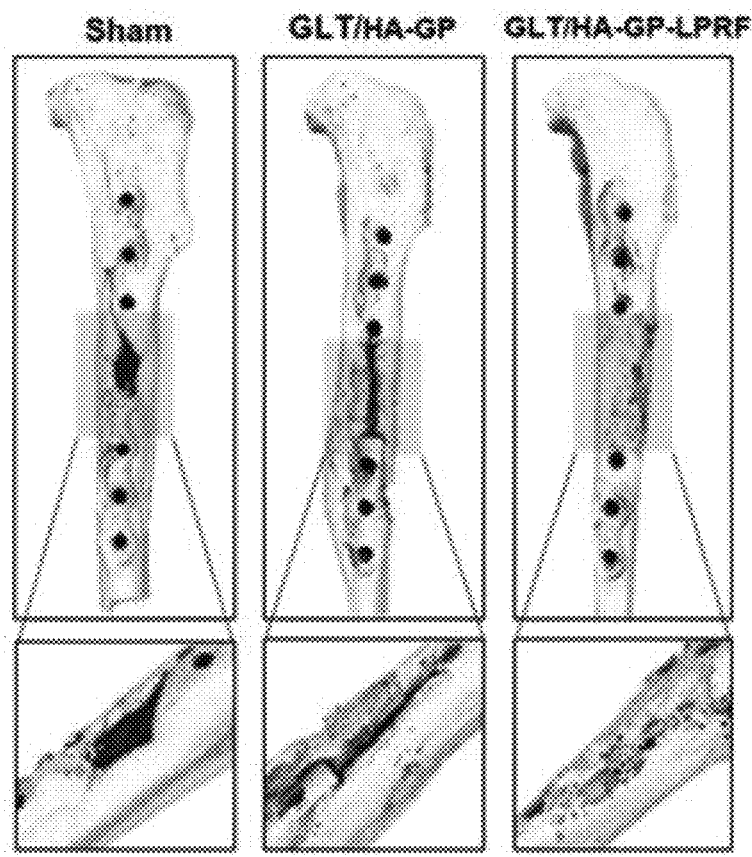
FIG. 17 shows another micro-CT images of rabbit tibia implanted with the hydrogels according to the invention.
Figure 18:
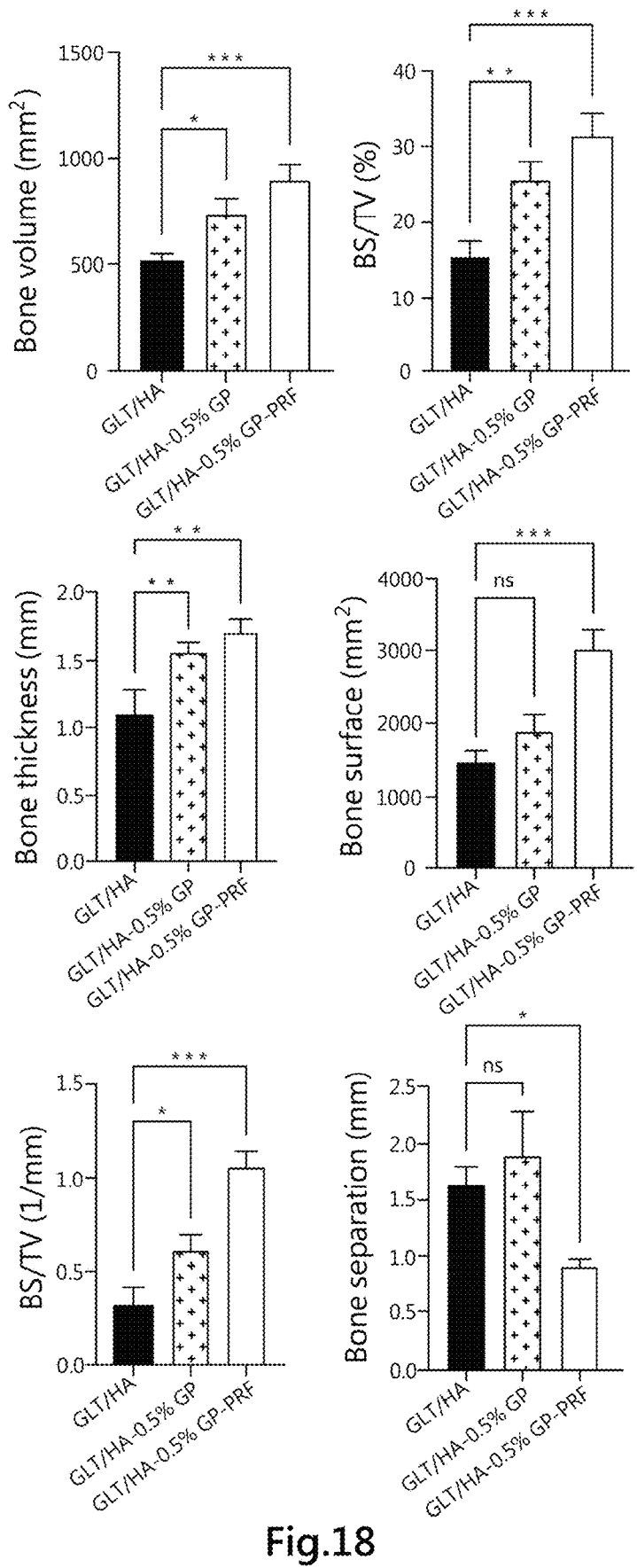
FIG. 18 shows quantitative CT analysis of rabbit tibia implanted with the hydrogels according to the invention.

On the contrary, significant new bone formation was found at the tibial bone defects in the GLT/HA-GP-LPRF treated groups. In all three views, the newly formed bony tissues were well connected with the adjacent bony margins of the bony defect, as shown in FIG. 17. The quantitative CT analysis further shows that GLT/HA-GP-LPRF group achieved a notably greater extent of new bone formation in parameters of bone volume, trabecular bone volume fraction (BV/TV), bone thickness, bone surface, BS/TV, and bone separation (FIG. 18).

These in vivo data consistently indicate that the GP-crosslinked GLT/HA hydrogel can be used for delivering PRF to the bone defect site, where beneficial growth factors are released due to biodegradation of the hydrogel, thus promoting osteogenic differentiations and mineralization of osteoblasts. GP crosslinking can help maintaining the stability of the hydrogel to ensure sustained stimulation of MSCs and gradual release of growth factors.

Specimens were then processed for decalcification. For histological evaluation, samples were embedded in paraffin, and blocks were cut to serial thick sections (around 5 μm for each slide). Tissue sections were then stained by hematoxylin and eosin (H&E), Alizarin red S (ARS) and immunohistochemical staining using type I collagen (Col 1) antibody. Specimen sections were also observed under light microscopy (Leica) to evaluate new bone formation.

Figure 19A:
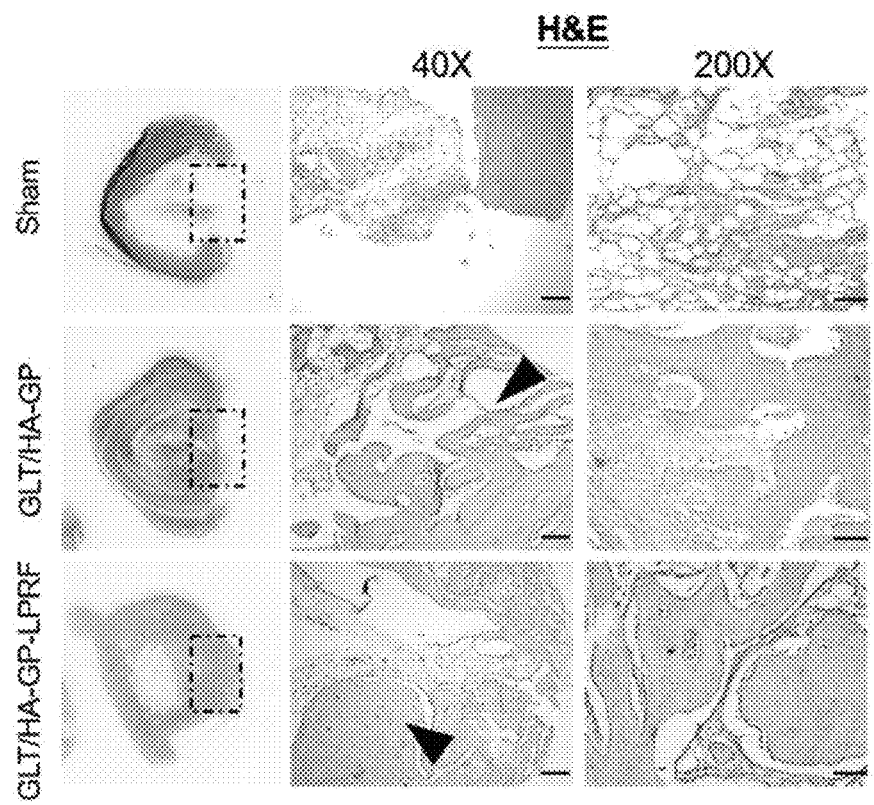
FIGS. 19A-19C are histological images showing tibial bone defect healing in the rabbit model at 8-week post-surgery, wherein bone tissue specimens are stained by Hematoxylin and eosin (H&E), Alizarin red S (ARS) and immunohistochemical staining (Col I), respectively, and the black dotted square boxes indicate defect regions and the black arrowheads indicate new bone formation at the defect site (40×-Scale bar-200 μm; 200×-50 μm).
Figure 19B:
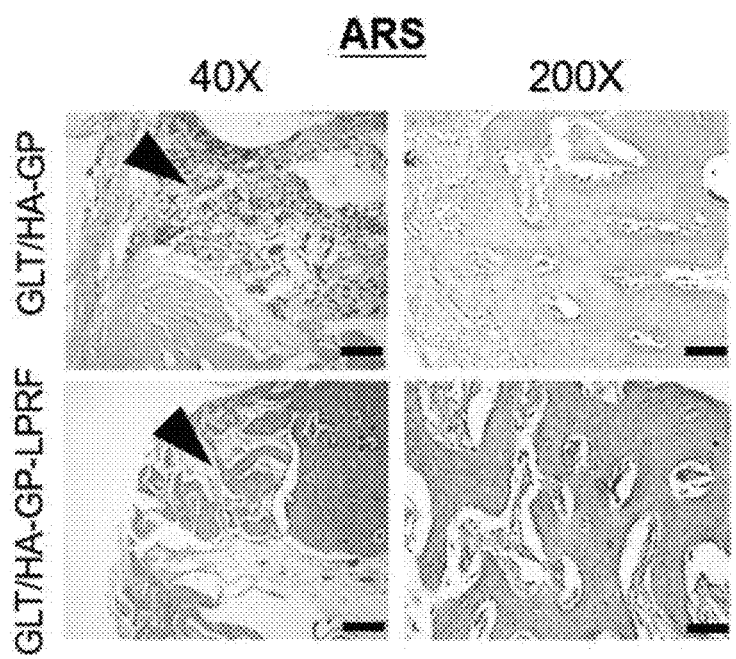
Figure 19C:
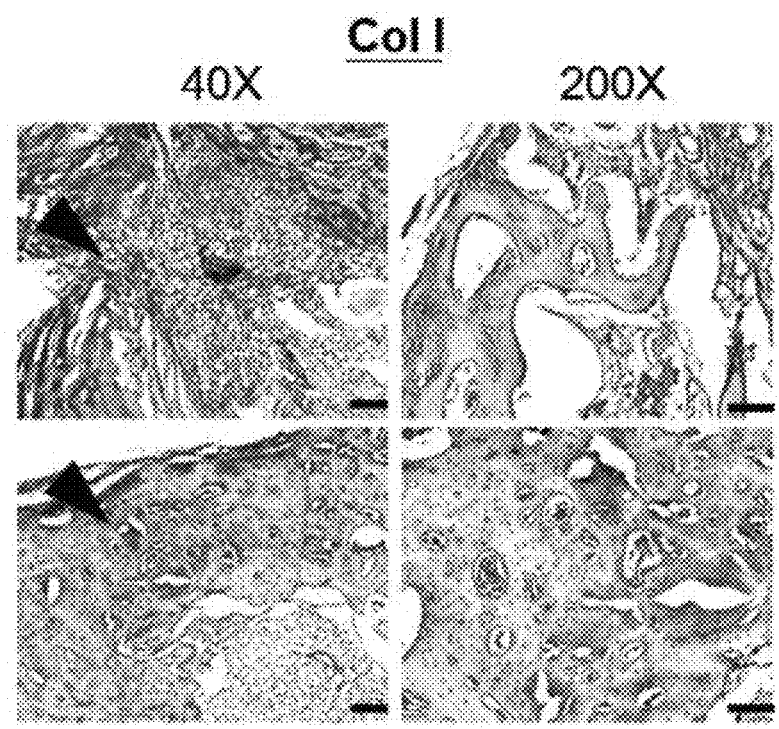

After 8 weeks of surgery, the defect remained clearly visible in the control sham group without evidence of tissue healing (FIG. 19A, upper panel). The results further confirmed that this surgically created rabbit tibial segmental bone defect could not be inherently repaired. In the GLT/HA-0.5% GP group, tiny amount of neobone was detected along the margin of the tibial bone defect (FIG. 19A, middle panel). Under higher magnification, the defect center was occupied with fibrous and immature bony tissues with higher cellularity and less organized matrix pattern. In contrast, histology showed that the defect was bridged and dense new bone formation were observed at the bone edges of the tibial defect in GLT/HA-0.5% GP-LPRF group. These newly formed bone tissues displayed more mature trabeculation, where cells resided in had more flattened lacunae and lamellar appearance than cells in the GLT/HA-0.5% GP group (FIG. 19A, lower panel). As shown in FIGS. 19B and 19C, the Alizarin red S (ARS) and immunohistochemical staining using type I collagen (Col 1) revealed that neobone tissues in GLT/HA-0.5% GP-LPRF group synthesized significantly more mineralized matrix than did the GLT/HA-0.5% GP group. When the histological results of ARS and Col I staining were combined, more mature woven bone formation was observed, particularly in GLT/HA-0.5% GP-LPRF bone tissue specimens.

All of the data disclosed in this Example suggest that GLT/HA-0.5% GP-LPRF hydrogel may serve as an osteoconductive biomaterial to allow ingrowth of osteoprogenitor cells from marrow and adjacent bony bed into the 3D structure of the porous scaffold.

While the invention has been described with reference to the preferred embodiments above, it should be recognized that the preferred embodiments are given for the purpose of illustration only and are not intended to limit the scope of the present invention and that various modifications and changes, which will be apparent to those skilled in the relevant art, may be made without departing from the spirit and scope of the invention.

What is claimed is:

1. An injectable hydrogel precursor composition consisting of:
   about 10% by weight of gelatin, based on the total weight of the composition;
   about 0.5-2% by weight of hyaluronic acid, based on the total weight of the composition;
   about 0.5-1.0% by weight of genipin, based on the total weight of the composition; and
   an aqueous medium having a pH ranging from 6-8;
   wherein the injectable hydrogel precursor composition is in form of a clear solution through mixing and adapted to transition into a hydrogel at 37° C. with a gelation time ranging from 10 minutes to 40 minutes while remaining injectable at room temperature for at least 60 minutes, and the hydrogel has a compressive strength ranging from 300 kPa to 500 kPa.

2. The injectable hydrogel precursor composition according to claim 1, wherein hyaluronic acid is in an amount of about 1% by weight based on the total weight of the composition, and genipin is in an amount of about 0.5% by weight based on the total weight of the composition.

3. The injectable hydrogel precursor composition according to claim 2, wherein the hyaluronic acid has a molecular weight of between about 8,000 kDa to about 10,000 kDa.

4. The injectable hydrogel precursor composition according to claim 3, wherein gelatin is selected from the group consisting of type-A gelatin, type-B gelatin, and a combination thereof.

5. The injectable hydrogel precursor composition according to claim 4, wherein gelatin comprises type-B gelatin.

6. The injectable hydrogel precursor composition according to claim 1, wherein the aqueous medium is selected from the group consisting of water, water-based solutions and water-based buffers.

7. A medical formulation comprising the injectable hydrogel precursor composition according to claim 1 in combination with an osteogenic substance selected from the group consisting of a mesenchymal stem cell, a stem cell secretome, a platelet-rich fibrin, a platelet-rich plasma, a chemotherapeutic drug, a growth factor, a cytokine, an antibiotic and a combination thereof.

8. A method for treating a segmental bone defect in a patient having a defect site between a first bone end and a second bone end disconnected to the first bone end, comprising injecting the medical formulation according to claim 7 to the defect site and allowing the medical formulation to transition to a hydrogel in situ.

9. The method according to claim 8, wherein the segmental bone defect is a critical segmental bone defect.

10. The method according to claim 9, wherein the patient is a human patient.

* * * * *